(12) United States Patent
Wands et al.

(10) Patent No.: US 7,078,500 B1
(45) Date of Patent: Jul. 18, 2006

(54) GENETIC IMMUNIZATION WITH NONSTRUCTURAL PROTEINS OF HEPATITIS C VIRUS

(75) Inventors: Jack Wands, Waban, MA (US); Jens Encke, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/600,493

(22) PCT Filed: Jan. 28, 1999

(86) PCT No.: PCT/US99/01823

§ 371 (c)(1),
(2), (4) Date: Jul. 18, 2000

(87) PCT Pub. No.: WO99/38880

PCT Pub. Date: Aug. 5, 1999

Related U.S. Application Data

(60) Provisional application No. 60/073,156, filed on Jan. 30, 1998.

(51) Int. Cl.
   *C12N 15/11* (2006.01)
(52) U.S. Cl. .................. 536/23.1; 435/325; 435/455
(58) Field of Classification Search ............... 536/23.1; 514/44; 435/235.1; 424/93.2
   See application file for complete search history.

(56) References Cited

U.S. PATENT DOCUMENTS

| | | | |
|---|---|---|---|
| 5,371,017 A * | 12/1994 | Houghton et al. ........ | 435/320.1 |
| 5,593,972 A | 1/1997 | Weiner et al. ................ | 514/44 |
| 5,739,118 A | 4/1998 | Carrano et al. ............... | 514/44 |
| 5,830,875 A | 11/1998 | Weiner et al. ................ | 514/44 |
| 6,025,341 A * | 2/2000 | Wands et al. | |
| 6,297,048 B1 * | 10/2001 | Jolly et al. | |
| 2002/0183508 A1 * | 12/2002 | Maertens et al. ........ | 536/23.72 |

FOREIGN PATENT DOCUMENTS

| WO | WO 96/13590 | * | 5/1996 |
| WO | WO 96/37606 | | 11/1996 |
| WO | WO 96/38474 | * | 12/1996 |
| WO | WO 97/47358 | | 12/1997 |
| WO | WO 99/29843 | | 6/1999 |

OTHER PUBLICATIONS

Houghton. M Strategies and Prospects for Vaccination Against Hepatitis C (1999) in Current Topics in Microbiolgy and Immunology pp. 327-339.*
Farci. P et al Prevention of hepatitis C infection in chimpanzees by hyperimmune serum against the hypervariable region 1 of the envelope proteins (1996) PNAS 93 15394-99.*
Selby et al Expression identification and subcellular localization of the protein encoded by the hepatitis C viral genome (1993) J Gen Virol 74 1103-1113.*
D Souza et al In vitro cleavage of hepattitis C polyprotein substrates by purified recombinant NS3 protesase (1995) J Gen Virol 76 1729-36.*
Harada et al Characterization of an established human hepatoma cell line constituitively expressing non-structural proteins of hepatitis C by transfection of viral cDNA (1995) J Gen Virol 76 1215-1221.*
Hartikka et al. An improved plasmid DNA expression vector for direct injection into skeletal muscle (1996) Human Gene Therapy 7 1205-1217.*
Selden RF, Transfection using DEAE dextran in Current Protocols in Molecular Biology Ausbel FM et al ed's (1987) John Wiley and Sons New York.*
Chattergoon M et al. Genetic Immunization a new era in vaccines and immune therapeutics (1997) FASEB J 10 753-63.*
McDonnell WM Molecular Medicine (1996) New Eng J Med. vol. 334, No. 1 42-45.*
Encke et al., Genetic Immunization Generates Cellular and Humoral Immune Response . . . , 1998, pp. 4917-4923.*
Kozak et al. (1999) Intiaition of translation in prokaryotes and eukaryotes GENE 234:187-208.*
Lieto et al. (2003) Human CD94 Gene Expression:Dual Promoters Differing in Responsiveness to IL-2 or IL-15. J. Immunol. 171:5277-5286.*
Martell, et al.; "Hepatitis C Virus (HCV) Circulates as a Population of Different but Closely Related Genomes: Quasispecies Nature of HCV Genome Distribution," *J. of Virol.*, 1992, vol. 66, No. 5, pp. 3225-3229.
Chisari, "Perspectives Series: Host/Pathogen Interactions,", *J. Clin. Invest.*, 1997, vol. 99, No. 7, pp. 1472-1477.
Rehermann, et al., Quantitative Analysis of the Peripheral Blood Cytotoxic T Lymphocyte Response in Patients with chronic Hepatitis C Virus Infection, *J. Clin. Invest.*, 1996, vol. 98, No. 6, pp. 1432-1440.
Alter, et al., The Natural History of Community-Acquired Hepatitis C In The United States, *The New England Journal of Medicine*, 1992, vol. 327, No. 27, pp. 1899-1905.

(Continued)

*Primary Examiner*—Deborah Crouch
*Assistant Examiner*—Louis D Lieto
(74) *Attorney, Agent, or Firm*—Woodcock Washburn LLP

(57) ABSTRACT

Nucleic acid molecule that comprise a hepatitis C nonstructural protein including specifically disclosed DNA sequences are disclosed. Pharmaceutical compositions that contain nucleic acid molecules comprising a hepatitis C nonstructural protein including a nucleotide sequence encoding NS3, NS4, or NS5, or a combination thereof, operably linked to regulatory elements functional in human cells are disclosed. Methods of immunizing individuals susceptible to or infected by hepatitis C virus comprising administering such pharmaceutical compositions are disclosed.

13 Claims, 8 Drawing Sheets

OTHER PUBLICATIONS

Tsukuma, et al., "Risk Factors For Hepatocellular Carcinoma Among Patients With Chronic Liver Disease", *The New England Journal of Medicine*, 1993, vol. 328, No. 25, pp. 1797-1801.

Xiang, et al., "Vaccination with a Plasmid Vector Carrying the Rabies Virus Glycoprotein Gene Induces Protective Immunity against Rabies Virus"; *Virol.*, 1994, vol. 199, pp. 132-140.

Ulmer, et al., "Heterologous Protection Against Influenza by Injection of DNA Encoding a Viral Protein", *Science*, 1993, vol. 259, pp. 1745-1749.

Wolff, et al., "Direct Gene Transfer into Mouse Muscle in Vivo," *Science*, 1990, vol. 247, pp. 1465-1468.

Choo, et al., "Isolation of a cDNA Clone Derived from a Blood-Borne Non-A, Non-B Viral Hepatitis Genome," *Science*, 1989, vol. 244, pp. 359-362.

Wang, et al., "Gene Inoculation Generates Immune Responses Against Human Immunodeficiency Virus Type 1"; *Proc. Natl. Acad. Sci. USA*, 1993, vol. 90, pp. 4156-4160.

Bukh, et al., "Sequence Analysis of the 5' Noncoding Region of Hepatitis C Virus," *Proc. Natl. Acad. Sci. USA*, 1992, vol. 89, pp. 4942-4946.

Inchaupse, et al., "Genomic Structure of the Human Prototype Strain H of Hepatitis C Virus: Comparison With American and Japanese Isolates," *Proc. Natl. Acad. Sci. USA*, 1991, vol. 88, pp. 10292-10292.

Choo, et al., "Genetic Organization and Diversity of the Hepatitis C Virus," *Proc. Natl. Acad. Sci. USA*, 1991, vol. 88, pp. 2451-2455.

Han, et al., "Characterization of the Terminal Regions of Hepatitis C Viral RNA: Identification of Conserved Sequences in the 5' Untranslated Region and Poly(A) Tails at the 3' End," *Proc. Natl. Acad. Sci. USA*, 1991, vol. 88, pp. 1711-1715.

Kato, et al. "Molecular Cloning of the Human Hepatitis C Virus Genome From Japanese Patients With Non-A, Non-B Hepatitis," *Proc. Nat'l. Acad. Sci.*, 1990, pp. 9524-9528.

Saito, et al., "Hepatitis C Virus Infection is Associated With The Development of Hepatocellular Carcinoma," *Proc. Natl. Acad. Sci. USA*, 1990, vol. 87, pp. 6547-6549.

Manthorpe, et al., "Gene Therapy by Intramuscular Injection of Plasmid DNA: Studies on Firefly Luciferase Gene Expression in Mice," *Vical, Inc., Human Gene Therapy*, 1993, 4:419-431.

Heintges, et al., "Hepatitis C Virus: Epidemiology and Transmission," *Hepatology*, 1997, vol. 26, No. 3, pp. 521-526.

Tokushige, et al., "Expression and Immune Response to Hepatitis C Virus Core DNA—Based Vaccine Constructs," *Hepatology*, 1996, vol. 24, No. 1, pp. 14-20.

Ferrari, et al., "T-Cell Response to Structural and Nonstructural Hepatitis C Virus Antigens in Persistent and Self-limited Hepatitis C Virus Infections," *Hepatology*, 1994, vol. 19, No. 2, pp. 286-295.

Kita, et al., "HLA B44-restricted Cytotoxic T Lymphocytes Recognizing an Epitope on Hepatitis C Virus Nucleocapsid Protein," *Hepatology*, 1993, vol. 18, No. 5, pp. 1039-1044.

Simonetti, et al. "Hepatitis C Virus Infection as a Risk Factor for Hepatocellular Carcinoma in Patients with Cirrhosis," *Annals of Internal Medicine*, 1992, vol. 116, No. 2, pp. 97-102.

Carithers, et al. "Therapy of Hepatitis C: Meta-analysis of Interferon Alfa-2b Trials," *Hepatology*, 1997, vol. 26, No. 3, pp. 83S-88S.

Tascon, et al., "Vaccination Against Tuberculosis by DNA Injection," *Nature Medicine*, 1996, vol. 2, No. 8, pp. 888-892.

Donnelly, et al., "Preclinical Efficacy of a Prototype DNA Vaccine: Enhanced Protection Against Antigenic Drift in Influenza Virus," *Nature Medicine*, 1995, vol. 1, No. 6, pp. 583-587.

Diepolder, et al., "Possible Mechanism Involving T-lymphocyte Response to Non-Structural Protein 3 in Viral Clearance in Acute Hepatitis C Virus Infection," *The Lancet*, 1995, vol. 346, pp. 1006-1007.

Boyer, et al. "Protection of Chimpanzees From High-Dose Heterologous HIV-1 Challenge by DNA Vaccination," *Nature Medicine*, 1997, vol. 3, No. 5, pp. 526-532.

Tang, et al., "Genetic immunization is a simple method for eliciting an immune response," *Nature*, 1992, vol. 356, pp. 152-154.

Wolff, et al., "Long-Term Persistence of Plasmid DNA and Foreign Gene Expression in Mouse Muscle," *Human Molecular Genetics*, 1992, vol. 1, No. 6, pp. 363-369.

Wang, et al., "DNA Inoculation Induces Neutralizing Immune Responses Against Human Immunodeficiency Virus Type 1 in Mice and Nonhuman Primates," *DNA and Cell Biology*, 1993, vol. 12, No. 9, pp. 799-805.

Fynan, et al., "Use of DNA Encoding Influenza Hemagglutinin as an Avian Influenza Vaccine," *DNA and Cell Biology*, 1993, vol. 12, No. 9, pp. 785-789.

Montgomery, et al., "Heterologous and Homologous Protection Against Influenza A by DNA Vaccination: Optimization of DNA Vectors," *DNA and Cell Biology*, 1993, vol. 12, No. 9, pp. 777-783.

Yankauckas, et al., "Long-Term Anti-Nucleoprotein Cellular and Humoral Immunity Is Induced by Intramuscular Injection of Plasmid DNA Containing NP Gene," *DNA and Cell Biology*, 1993, vol. 12, No. 9, pp. 771-776.

Xiang, et al., "Manipulation of the Immune Response to a Plasmid-Encoded Viral Antigen by Coinoculation with Plasmids Expressing Cytokines," *Immunity*, 1995, vol. 2, pp. 129-135.

Koziel, et al., "Intrahepatic Cytotoxic T Lymphocytes Specific For Hepatitis C Virus in Person With Chronic Hepatitis," *J. of Immun.*, 1992, vol. 149, No. 10, pp. 3339-3344.

Nelson, et al., "The Role of Hepatitis C Virus-Specific Cytotoxic T Lymphocytes in Chronic Hepatitis C[1]," *J. of Immun.*, 1997, vol. 158, pp. 1473-1481.

Geissler, et al., "Enhancement of Cellular and Humoral Immune Responses to Hepatitis C Virus Core Protein Using DNA-Based Vaccines Augmented with Cytokine-Expressing Plasmids[1]," *J. of Immun.*, 1997, vol. 158, pp. 1231-1237.

Okamoto, et al., "Nucleotide Sequence of the Genomic RNA of Hepatitis C Virus Isolated From a Human Carrier: Comparison With Reported Isolates for Conversed and Divergent Regions," *J. of Gen. Virol.*, 1991, vol. 72, pp. 2697-2704.

Selby, et al., "Expression, identification and subcellular localization of the proteins encoded by the hepatitis C viral genome," *J. of Gen. Virol.*, 1993, vol. 74, pp. 1103-1113.

Simmonds, et al., "Classification of hepatitis C virus into six major genotypes and a series of subtypes by phylogenetic analysis of the NS-5 region," *Journal of General Virology*, 1993, vol. 74, pp. 2391-2399.

Grakoui, et al., "Characterization of the Hepatitis C Virus-Encoded Serine Proteinase: Determination of Proteinase- Dependent Polyprotein Cleavage Sites," *Journal of Virology*, 1993, vol. 67, No. 5, pp. 2832-2843.

Bartenschlager, et al., "Nonstructural Protein 3 of the Hepatitis C Virus Encodes a Serine-Type Proteinase Required for Cleavage at the NS3/4 and NS4/5 Junctions," *Journal of Virology*, 1993, vol. 67, No. 7, pp. 3835-3844.

Missale, et al., "Different Clinical Behaviors of Acute Hepatitis C Virus Infection Are Associated with Different Vigor of the Anti-viral Cell-mediated Immune Response," *J. Clin. Invest.*, 1996, vol. 98, No. 3, pp. 706-714.

Barry, et al., "Production of Monoclonal Antibodies by Genetic Immunication," *Short Technical Reports*, 1994, vol. 16, No. 4, pp. 616-619.

Heinz et al., "Comparative Molecular Biology of Faviviruses and Hepatitis C Virus" *Arch Viorol.*, 1992, [Suppl] 4, pp. 163-171.

Viral Hepatitis and Liver Disease, Proceedings of the International Symposium on Viral Hepatitis and Liver Disease: Molecules Today, More Cures Tomorrow, Nishioka et al. Eds., Tokyo, May 10-14, 1993 (1993 ISVHLD).

Encke, J., et al., "Genetic immunization generates cellular and humoral immune responses against the nonstructural proteins of the hepatitis C. virus in a murine model," *J. Immunology*, Nov. 1, 1998, XP-002233910, 161(9), 4917-4923.

Inchauspe, G., "Gene vaccination for hepatitis C," *Springer Seminars in Immunopathology*, 1997, XP008014824, 19(2), 211-221.

Papa, S., et al., "Development of a multigenic plasmid vector for HCV DNA immunization," *Research in Virology*, Sep. 1998, XP002233911, 149(5), 315-319.

Saito, T., et al., "Plasmid DNA-based immunization for hepatitis C virus structural proteins: immune responses in mice," *Gastroenterology*, Apr. 1997, XP001013414, XP001013414, 112(4), 1321-1330.

Stuyver, L., et al., "Cloning and phylogenetic analysis of the core, E2, and NS3/NS4 regions of the hepatitis C virus type 5A+," 1994, BBRC 202(3), 1308-1314.

Yoo, et al., "5' End-Dependent Translation Initiation of Hepatitis C Viral RNA and the Presence of Putative Positive and Negative Translational Control Elements with the 5' Untranslated Region", *Virology 191*, 889-899, 1992.

Inchauspé, G., "Mechanisms of Protection in Hepatitis C Virus Infection," *Med. Mal. Infect.*, 1995, 25, 1067-1073.

US 6,180,768, 01/2001, Maertens et al. (withdrawn)*

* cited by examiner

| IMMUNIZATION | TUMOR CHALLENGE | TUMOR FORMATION | TUMOR WEIGHT (in g +/- SD) |
|---|---|---|---|
| 100 μg Mock DNA | 3 x i.m. SP/2NS5-21 | 10/10 (100%) | 1.9 +/- 0.2 |
| 100 μg pApNS5 DNA | 3 x i.m. SP/2NS5-21 | 8/20 (40%) | 0.7 +/- 0.1 |
| 100 μg pApNS5 DNA | 3 x i.m. SP/2-19 | 9/10 (90%) | 2.2 +/- 0.5 |
| 5 μg RECOMB. PROTEIN | 3 x i.p. SP/2NS5-21 | 10/10 (100%) | 1.9 +/- 0.2 |
| 100 μg pApNS5 DNA 5 μg RECOMB. PROTEIN | 2 x i.m. 1 x i.p. SP/2NS5-21 | 7/10 (70%) | 1.1 +/- 0.2 |

FIG.4A

GENETIC IMMUNIZATION WITH NONSTRUCTURAL PROTEINS OF HEPATITIS C VIRUS

CROSS-REFERENCE TO RELATED APPLICATIONS

The present application claims benefit of international application No. PCT/US99/01823 filed on Jan. 28, 1999, which was published under PCT Article 21(2) in English, which claims priority to Ser. No. 60/073,156 filed Jan. 30, 1998, each of which is incorporated herein by reference in its entirety.

FIELD OF THE INVENTION

The present invention relates to recombinant nucleic acid molecules, and pharmaceutical compositions comprising the same, which are useful as, for example, anti-hepatitis C virus vaccine components in genetic immunization protocols, to methods of inducing an immune response against hepatitis C virus infection and to methods of treating individuals suffering from hepatitis C virus infection.

BACKGROUND OF THE INVENTION

Hepatitis C virus (HCV), the major etiologic agent of transfusion acquired non-A, non-B hepatitis, is responsible for approximately 150,000 new cases of acute viral hepatitis annually in the United States. Choo, et al., *Science,* 1989, 244, 359–362. There is a prevalence of 0.6 to 2.0% in western countries and up to 15% in some underdeveloped regions of the world. Heintges, et al., *Hepatology,* 1997, 26, 521–526. Approximately half of these infections progress to a chronic infection that can be associated with cirrhosis and/or hepatocellular carcinoma (Alter, et al., *Science,* 1992, 258, 135–140; and Alter, et al., *New Eng. J. Med.,* 1992, 327, 1899–1905). In addition, HCV infection is an independent risk factor for the development of hepatocellular carcinoma as shown by the prevalence of anti-HCV antibodies (Colombo, et al., *Lancet,* 1989, ii, 1006–1008; Saito, et al., *Proc. Natl. Acad. Sci. USA,* 1990, 87, 6547–6549, Simonetti, et al., *An. Int. Med.,* 1992, 116, 97–102; and Tsukuma, et al., *New Eng. J. Med.,* 1993, 328, 1797–1801).

HCV is an enveloped, positive stranded RNA virus, approximately 9,500 nucleotides in length, which has recently been classified as a separate genus within the Flavivirus family. Heinz, *Arch. Virol. (Suppl.),* 1992, 4, 163–171. Different isolates show considerable nucleotide sequence diversity leading to the subdivision of HCV genomes into at least eight genotypes. Simmonds, et al., *J. Gen. Virol.,* 1993, 74, 2391–2399. In all genotypes, the viral genome contains a large open reading frame (ORF) that encodes a precursor polyprotein of 3010 to 3033 amino acids of approximately 330 Kd. Choo, et al., *Proc. Natl. Acad. Sci. USA,* 1991, 88, 2451–2455; Inchauspe, et al., *Proc. Natl. Acad. Sci. USA,* 1991, 88, 10292–10296; Kato, et al., *Proc. Natl. Acad. Sci. USA,* 1990, 87, 9524–9528; Okamoto. et al., *J. Gen. Virol.,* 1991, 72, 2697–2704; and Takamizawa, et al., *J. Gen. Virol.,* 1991, 65, 1105–1113.

Individual HCV polypeptides are produced by proteolytic processing of the precursor polypeptide to produce core (C), envelope (E1, E2) and non-structural (NS2–NS5) proteins. Bartenschlager, et al., *J. Gen. Virol.,* 1993, 67, 3835–3844; Grakoui, et al., *J. Gen. Virol.,* 1993, 67, 2832–2843; and Selby, et al., *J. Gen. Virol.,* 1993, 74, 1103–1113. This proteolysis is catalyzed by a combination of both cellular and viral encoded proteases. The NS3 gene encodes for a serine protease which cleaves the viral polyprotein precursor post-transcriptionally at several functions and also serves as the viral helicase. The NS5 region encodes for the RNA-dependent RNA-Polymerase of the virus.

In addition to the translated region, the HCV genome also contains both a 5' untranslated region (5' UTR) and a 3' untranslated region (3' UTR). The 5' UTR of 324 to 341 nucleotides represents the most highly conserved sequence among all HCV isolates reported to date. Han, et al., *Proc. Natl. Acad. Sci. USA,* 1991, 88, 1711–1715; and Bukh, et al., *Proc. Natl. Acad. Sci. USA,* 1992, 89, 4942–4946. This 5' UTR has been postulated to contain important regulatory elements for replication and/or translation of HCV RNAs. The 5' UTR also contains several small open reading frames (ORF) but there is presently no evidence to suggest that these ORF sequences are actually translated.

The cellular immune events involved in liver damage and viral clearance during HCV infection have only partially been defined. In an attempt to examine a potential pathogenic role of liver-infiltrating lymphocytes in patients with chronic HCV infection, Koziel, et al. examined the cytotoxic T lymphocyte (CTL) response of such cells and demonstrated an HLA class I-restricted CD8+ CTL response that was directed against both structural and non-structural regions of HCV polypeptides. Koziel, et al., *J. Virol.,* 1993, 67, 7522–7532; and Koziel, et al., *J. Immunol.,* 1992, 149, 3339–3344. Other investigators have also noted the existence of CTLs in peripheral blood mononuclear cell populations that recognize epitopes on core and the other viral related proteins during chronic HCV infection. Kita, et al., *Hepatol.,* 1993, 18, 1039–1044; and Cerny, et al., *Intl. Symp. Viral Hepatitis Liver Dis.,* 1993, 83 (abstr.). Botarelli, et al. (Botarelli, et al., *Gastroenterol.,* 1993, 104, 580–587) and Ferrari, et al. (Ferrari, et al., *Hepatol.,* 1994, 19, 286–295) found HLA class II-restricted CD4+ T cell-mediated proliferative responses to several recombinant proteins derived from different regions of HCV in patients with chronic HCV infection.

During active HCV infection, humoral and cellular immune responses have been shown to be polyclonal and multispecific and it is likely that the host immune response produced during persistent HCV infection is responsible, in part, for production of the liver cell injury. However, these immune responses may not be sufficiently broad based or vigorous enough to promote viral clearance and generate protective immunity in individuals with chronic HCV infection. Chisari, *J. Clin. Invest.,* 1997, 99, 1472–1477. Those individuals who have recovered from acute HCV infection have recently been shown to develop strong proliferative CD4+ T cell responses directed against peptide derived from the nonstructural proteins. Missale, et al., *J. Clin. Invest.,* 1996, 98, 706–714; and Diepolder, et al., *Lancet,* 1995, 346, 1006–1007. More important, the generation of HCV specific CTL activity appears to be associated with control of viral replication in individuals with chronic hepatitis. Rehermann, et al., *J. Clin. Invest.,* 1996, 98, 1432–1440; and Nelson, et al., *J. Immunol.,* 1997, 158, 1473–1481.

However, it is unknown if the nonstructural proteins NS3, NS4 and NS5 are sufficiently immunogenic to generate broad based and vigorous CTL-responses in vivo.

Presently, there is no universal, highly effective therapy of chronic HCV infection. Development of a vaccine strategy for HCV is complicated not only by the significant heterogeneity among HCV isolates, but also by the mixture of heterogeneous genomes within an isolate. Martell, et al., *J. Virol.,* 1992, 66, 3225. In addition, the virus contains a highly variable envelope region. Effective therapy has been limited only to interferons. Carithers, et al., *Hepatology*, 1997, 26, 83S–88S. Indeed, approximately 8–10% of individuals treated with such agents respond and irradicate HCV from the liver. However, recent studies have revealed that individuals who recover from acute HCV infection develop substantial CD4+ T-cell proliferative responses against the nonstructural proteins as compared to those individuals who acquire persistent HCV infection. Missale, et al., *J. Clin. Invest.*, 1996, 98, 706–714; and Diepolder, et al., *Lancet*, 1995, 346, 006–1007.

Direct injection of DNA into animals is a promising method for delivering specific antigens for immunization. Barry, et al., *Bio Techniques*, 1994, 16, 616–619; Davis, et al., *Hum. Mol. Genet.*, 1993, 11, 1847–1851; Tang, et al., *Nature*, 1992, 356, 152–154; Wang, et al., *J. Virol.*, 1993, 67, 3338–3344; and Wolff, et al., *Science*, 1990, 247, 1465–1468. This approach has been successfully used to generate protective immunity against influenza virus in mice and chickens, against bovine herpes virus I in mice and cattle and against rabies virus in mice. Cox, et al., *J. Virol.*, 1993, 67, 5664–5667; Fynan, et al., *DNA and Cell Biol.*, 1993, 12, 785–789; Ulmer, et al., *Science*, 1993, 259, 1745–1749; and Xiang, et al., *Virol.*, 1994, 199, 132–140. In most cases, strong, yet highly variable, antibody and cytotoxic T-cell responses were associated with control of infection. Indeed, the potential to generate long-lasting memory CTLs without using a liver vector makes this approach particularly attractive compared with those involving killed-virus vaccines and generating a CTL response that not only protects against acute infection but also may have benefits in eradicating persistent viral infection. Wolff, et al., *Science*, 1990, 247, 1465–1468; Wolff. et al., *Hum. Mol. Genet.*, 1992, 1, 363–369; Manthorpe, et al., *Human Gene Therapy*, 1993, 4, 419–431; Ulmer, et al., *Science*, 1993, 259, 1745–1749; Yankauckas, et al., *DNA and Cell Biol.*, 1993, 12, 777–783; Montgomery, et al., *DNA and Cell Biol.*, 1993, 12, 777–783; Fynan, et al., *DNA and Cell Biol.*, 1993, 12, 785–789; Wang, et al., *Proc. Natl. Acad. Sci. USA*, 1993, 90, 4156–4160; Wang, et al., *DNA and Cell Biol.*, 1993, 12, 799–805; Xiang, et al., *Virol.*, 1994, 199, 132–140; Davis, et al., *Hum. Mol. Genet.*, 1993, 11, 1847–1851; Donnelly, et al., *Nat. Med.*, 1995, 1, 583–587; Boyer, et al., *Nat. Med.*, 1997, 3, 526–532; Tascon, et al., *Nat. Med.*, 1996, 2, 888–892; and Huygen, et al., *Nat. Med.*, 1996, 2, 893–898. The advantage of this method compared to immunizations with soluble recombinant proteins or peptides is the ability to induce a strong inflammatory CD4+ T cell response as well as cytotoxic T cell activity, presumably due to the intracellular processing of viral proteins into peptides and subsequent loading on MHC class I molecules in transfected cells and yet to be defined interactions with antigen presenting cells. In contrast, immunization with soluble protein leads primarily to a humoral immune response due to precessing through the MHC class II pathway. Immunization with synthetic peptides has several disadvantages since only a limited number of epitopes are available for stimulation of the host immune response. In contrast, all naturally occurring B and T cell epitopes encoded for each protein by the DNA construct of interest are presumably preserved for recognition by T cell receptors and therefore will presumably generate very broad based humoral and cellular immune responses. McDonnell, et al., *N. Engl. J. Med.*, 1996, 334, 42–45.

Vaccination and immunization generally refer to the introduction of a non-virulent agent against which an individual's immune system can initiate an immune response which will then be available to defend against challenge by a pathogen. The immune system identifies invading "foreign" compositions and agents primarily by identifying proteins and other large molecules which are not normally present in the individual. The foreign protein represents a target against which the immune response is made.

PCT Patent Application PCT/US90/01348 discloses sequence information of clones of the HCV genome, amino acid sequences of HCV viral proteins and methods of making and using such compositions including anti-HCV vaccines comprising HCV proteins and peptides derived therefrom.

U.S. Pat. Nos. 5,830,876, 5,593,972, 5,739,118 and PCT Patent Application Serial Number PCT/US94/00899 filed Jan. 26, 1994, the disclosures of which are incorporated herein by reference in their entirety, each contain descriptions of genetic immunization protocols. Vaccines against HCV are disclosed in each.

There remains a need for vaccines useful to protect individuals against hepatitis C virus infection. There remains a need for methods of protecting individuals against hepatitis C virus infection.

SUMMARY OF THE INVENTION

The present invention relates to recombinant nucleic acid molecules comprising a nucleotide sequence that encodes a hepatitis C virus nonstructural protein, such as, for example, NS3, NS4, or NS5, or a combination thereof.

The present invention relates to pharmaceutical compositions comprising a recombinant nucleic acid molecule that comprises a nucleotide sequence that encodes a hepatitis C virus nonstructural protein. The nucleotide coding sequence that encodes the hepatitis C virus nonstructural protein is operably linked to regulatory elements functional in human cells. The pharmaceutical composition additionally comprises a pharmaceutically acceptable carrier or diluent, and optionally a facilitator such as, for example, bupivicaine.

The present invention relates to methods of immunizing an individual susceptible to hepatitis C virus comprising administering to such an individual, a pharmaceutical composition comprising a recombinant nucleic acid molecule which comprises a nucleotide coding sequence that encodes a hepatitis C virus nonstructural protein. The nucleotide coding sequence that encodes the hepatitis C virus nonstructural protein is operably linked to regulatory elements functional in human cells. The pharmaceutical composition additionally comprises a pharmaceutically acceptable carrier or diluent. The individual is administered an amount effective to induce a protective immune response against hepatitis C virus infection.

The present invention relates to methods of treating an individual having hepatitis C virus comprising administering to such an individual, a pharmaceutical composition comprising a recombinant nucleic acid molecule which comprises a nucleotide coding sequence that encodes a hepatitis C virus nonstructural protein. The nucleotide coding sequence that encodes the hepatitis C virus nonstructural protein is operably linked to regulatory elements functional in human cells. The pharmaceutical composition additionally comprises a pharmaceutically acceptable carrier or diluent. The individual is administered an amount effective to induce a therapeutic immune response against hepatitis C virus infection.

BRIEF DESCRIPTION OF THE FIGURES

FIG. 4A is a table showing representative results of a tumor model to assess CTL activity.

DESCRIPTION OF PREFERRED EMBODIMENTS OF THE INVENTION

Figure 1A:
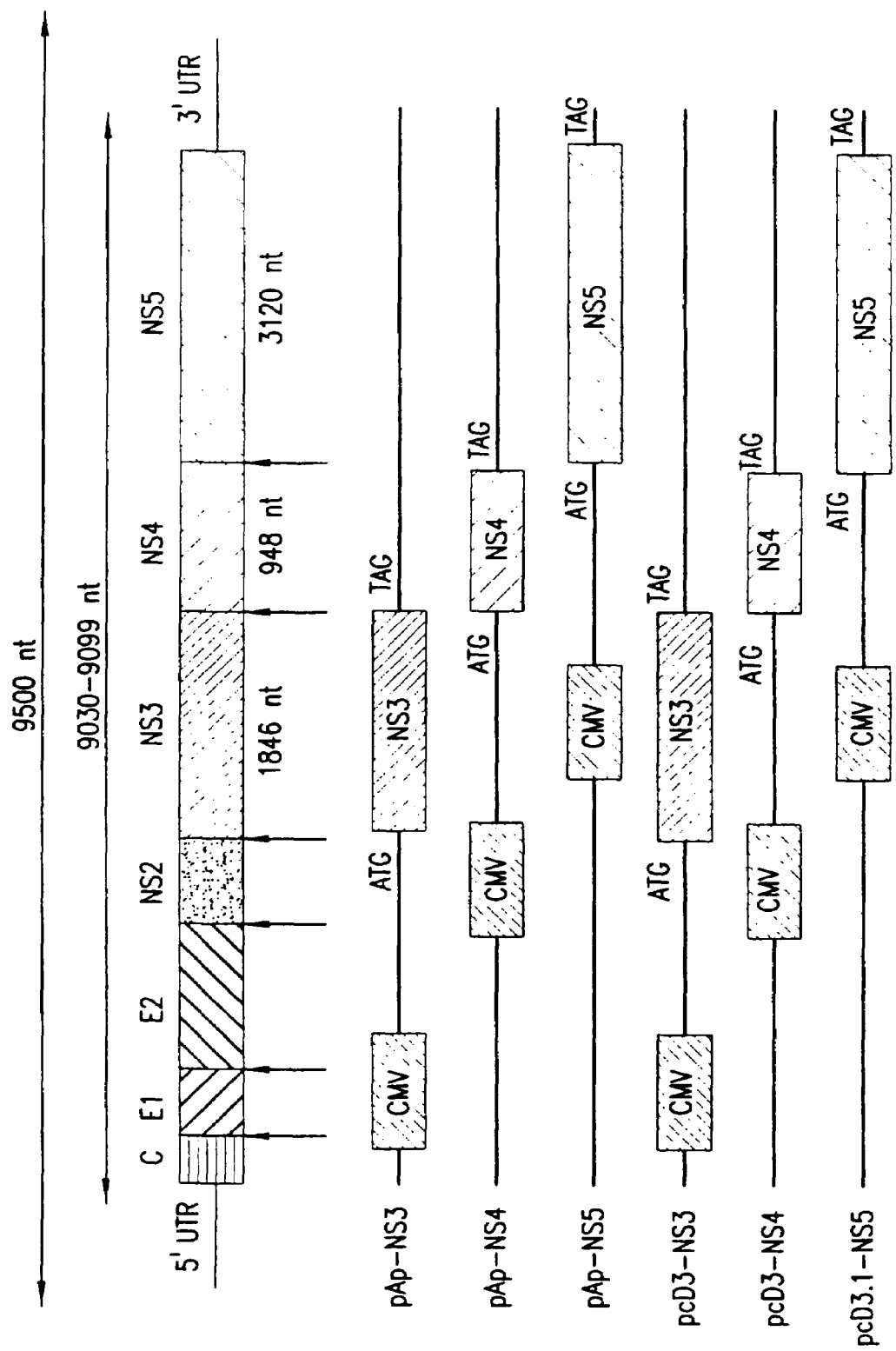
FIG. 1A shows a schematic illustrating a single large ORF of HCV encodes for a polyprotein precursor of about 3011–3030 aa which is cleaved by host signal and virus proteases into the different structural and nonstructural proteins, as shown by the arrows.

According to the present invention, compositions and methods are provided which prophylactically and/or therapeutically immunize or treat an individual against HCV infection. Recombinant nucleic acid molecules comprising a nucleotide coding sequence that encodes a HCV nonstructural protein, such as, for example, NS3, NS4, or NS5, or a combination thereof, are administered to the individual. The protein encoded by the recombinant nucleic acid gene construct is expressed by the individual's cells and serves as an immunogenic target against which an anti-HCV immune responses are elicited. The resulting immune responses are broad based; in addition to a humoral immune response, both arms of the cellular immune response are elicited. The methods of the present invention are useful for conferring prophylactic and therapeutic immunity. The methods of the present invention can also be practiced on mammals, other than humans, for biomedical research. Thus, the methods of the present invention can be employed to both immunize an individual from HCV challenge as well as treat an individual suffering from HCV infection.

As used herein, the phrase "HCV nonstructural protein" is meant to refer to HCV nonstructural proteins NS3, NS4, and NS5, and equivalents thereof. Equivalent proteins include peptide fragments of NS3, NS4, and NS5 which retain bioactivity as described herein. In addition, the term HCV nonstructural protein is meant to refer to corresponding HCV nonstructural proteins from additional HCV isolates which may vary in sequence. Those having ordinary skill in the art can readily identify the HCV nonstructural proteins from additional HCV isolates. It is to be understood that nucleotide substitutions in the codon may be acceptable when the same amino acid is encoded. In addition, it is also to be understood that nucleotide changes may be acceptable wherein conservative amino acid substitution(s) result from the nucleotide substitution(s). It is to be understood that the phrase "HCV nonstructural protein" also includes fusion proteins comprising the nonstructural protein, as well as therapeutically or prophylactically active fragments thereof.

As used herein, the phrase "gene construct" is meant to refer to a recombinant nucleic acid molecule comprising a nucleotide coding sequence that encodes a HCV nonstructural protein, as well as initiation and termination signals operably linked to regulatory elements including a promoter and polyadenylation signal capable of directing expression in the cells of the vaccinated individual. In some embodiments, the gene construct further comprises an enhancer, Kozak sequence (GCCGCCATG; SEQ ID NO:1), and at least a fragment of the HCV 5' UTR.

As used herein, the phrase "genetic vaccine" refers to a pharmaceutical preparation that comprises a gene construct. Genetic vaccines include pharmaceutical preparations useful to invoke a prophylactic and/or therapeutic immune response to HCV.

As used herein, the phrase "nucleic acid" refers to DNA, RNA, or chimeras formed therefrom.

According to the present invention, gene construct(s) are introduced into the cells of an individual where it is expressed, thus producing at least one HCV nonstructural protein. Preferably, the regulatory elements of the gene constructs of the invention are capable of directing expression in mammalian cells, preferably human cells. The regulatory elements include a promoter and a polyadenylation signal. In addition, other elements, such as an enhancer and a Kozak sequence, may also be included in the gene construct.

When taken up by a cell, the gene constructs of the invention may remain present in the cell as a functioning extrachromosomal molecule or it may integrate into the cell's chromosomal DNA. Nucleic acid, such as DNA, may be introduced into cells where it remains as separate genetic material in the form of a plasmid. Alternatively, linear nucleic acid that can integrate into the chromosome may be introduced into the cell. When introducing nucleic acid into the cell, reagents which promote nucleic acid integration into chromosomes may be added. DNA sequences which are useful to promote integration may also be included in the DNA molecule. Alternatively, RNA may be administered to the cell. It is also contemplated to provide the gene construct as a linear minichromosome including a centromere, telomeres and an origin of replication.

According to the present invention, the gene construct comprises recombinant nucleic acid molecules comprising a nucleotide coding sequence that encodes a HCV nonstructural protein. In some preferred embodiments, the recombinant nucleic acid molecule comprises a nucleotide coding sequence that encodes NS3. In other preferred embodiments, the recombinant nucleic acid molecule comprises a nucleotide coding sequence that encodes a HCV nonstructural protein that comprises NS4. In other preferred embodiments, the recombinant nucleic acid molecule comprises a nucleotide coding sequence that encodes a HCV nonstructural protein that comprises NS5. In other preferred embodiments, the recombinant nucleic acid molecule comprises a nucleotide coding sequence that encodes any combination of HCV nonstructural proteins including NS3, NS4, and NS5.

In some preferred embodiments, the recombinant nucleic acid molecule comprises a nucleotide coding sequence that encodes a HCV nonstructural protein that comprises a fragment of HCV NS3, NS4, or NS5 protein, or a combination thereof. The fragments include, but are not limited to, fragments containing 10, 25, 50, 75, 100, 150, 200, 250, 300, 350, 400, 450, 500, 550, 600, 650, 700, 750, 800, 850, 900, 950, or 1000 amino acids of the corresponding nonstructural protein. In addition, the fragment can comprise a portion of the carboxy terminus of the protein, amino terminus, or any portion therebetween. One skilled in the art can readily prepare immunogenic fragments of the HCV nonstructural proteins or fusion proteins containing immunogenic fragments of any combination of nonstructural proteins. Thus, it is contemplated that the recombinant nucleic acid molecule comprising a nucleotide coding sequence that encodes a HCV nonstructural protein may comprise less than the entire HCV nonstructural gene product without substantially altering the effectiveness of the vaccine. It is also contemplated that at least one nucleotide, as well as multiple, substitution may be made in the nucleotide coding sequence without affecting the amino acid sequence of the protein. It is also contemplated that at least one conservative amino acid substitution, as well as multiple substitutions, may be made throughout the protein without substantially reducing the immunogenic activity of the HCV nonstructural protein.

In some embodiments of the invention, the recombinant nucleic acid molecule comprises a fragment of the 5' UTR that includes the last 9 nucleotides of the HCV 5' UTR, the last 25 nucleotides of the HCV 5' UTR, the last 50 nucleotides of the HCV 5' UTR, the last 75 nucleotides of the HCV 5' UTR, the last 100 nucleotides of the HCV 5' UTR, the last 150 nucleotides of the HCV 5' UTR, the last 200 nucleotides of the HCV 5' UTR, the last 250 nucleotides of the HCV 5' UTR, or the last 300 nucleotides of the HCV 5' UTR. In some preferred embodiments, the gene construct includes the entire HCV 5' UTR. In some preferred embodiments, the gene construct includes the 9 most 3' nucleotides of the HCV 5' UTR. The entire HCV 5' UTR of a preferred embodiment is GCCAGCCCCC GATTGGGGGCGA-CACTCCACCATAGATCACTCCCCTGT-GAGGAACTACTGTCT TCACGCA-GAAAGCGTCTAGCCATGGCGTTAGTATGAGTGTC GTGCAG CCTCCAGGACCCCCCCTCCCGGGAGAGC-CATAGTGGTCTGCGGAACCGGT GAGTACACCG-GAATTGCCAGGACGACCGGGTCCTTTCT-TGGATCAACCCG CTCAATGCCTGGAGATTTGGGCGTGC-CCCCGCGAGACTGCTAGCCGAGTA GTGT-TGGGTCGCGAAAGGCCTTGTGGTACTGC-CTGATAGGGTGCTTGCGA GTGCCCCGGGAGGTCTCGTAGACCGTGCACC (SEQ ID NO:2).

The regulatory elements necessary for gene expression of a DNA molecule include: a promoter, an initiation codon, a stop codon, and a polyadenylation signal. In addition, enhancers are often required for gene expression. It is necessary that these elements be operably linked to the sequence that encodes the HCV nonstructural protein and that the regulatory elements are operable in the individual to whom they are administered. Initiation codons and stop codon are generally considered to be part of a nucleotide sequence that encodes the HCV nonstructural protein.

Promoters and polyadenylation signals used must be functional within the cells of the individual. In order to maximize protein production, regulatory sequences may be selected which are well suited for gene expression in the cells the construct is administered into. Moreover, codons may be selected which are most efficiently transcribed in the cell. One having ordinary skill in the art can produce DNA constructs which are functional in the mammalian, preferably human, cells.

Examples of promoters useful to practice the present invention, especially in the production of a genetic vaccine for humans, include but are not limited to promoters from Simian Virus 40 (SV40), Mouse Mammary Tumor Virus (MMTV) promoter, Human Immunodeficiency Virus (HIV) such as the HIV Long Terminal Repeat (LTR) promoter, Moloney virus, ALV, Cytomegalovirus (CMV) such as the CMV immediate early promoter, Epstein Barr Virus (EBV), Rous Sarcoma Virus (RSV) as well as promoters from human genes such as human Actin, human Myosin, human Hemoglobin, human muscle creatine and human metalothionein.

Examples of polyadenylation signals useful to practice the present invention, especially in the production of a genetic vaccine for humans, include but are not limited to SV40 polyadenylation signals and LTR polyadenylation signals. In particular, the SV40 polyadenylation signal which is in pCEP4 plasmid (Invitrogen, San Diego Calif.), referred to as the SV40 polyadenylation signal, is used.

In addition to the regulatory elements required for gene expression, other elements may also be included in a gene construct. Such additional elements include enhancers. The enhancer may be selected from the group including but not limited to: human Actin, human Myosin, human Hemoglobin, human muscle creatine and viral enhancers such as those from CMV, RSV and EBV.

Gene constructs can be provided with mammalian origin of replication in order to maintain the construct extrachromosomally and produce multiple copies of the construct in the cell. Plasmids pCEP4 and pREP4 from Invitrogen (San Diego, Calif.) contain the Epstein Barr virus origin of replication and nuclear antigen EBNA-1 coding region which produces high copy episomal replication without integration.

Routes of administration include, but are not limited to, intramuscular, intrapentoneal, intradermal, subcutaneous, intravenous, intraarterially, intraoccularly and oral as well as transdermally or by inhalation or suppository. Preferred routes of administration include intramuscular, intraperitoneal, intradermal and subcutaneous injection. Delivery of gene constructs which encode HCV nonstructural protein can confer mucosal immunity in individuals immunized by a mode of administration in which the material is presented in tissues associated with mucosal immunity. Thus, in some examples, the gene construct is delivered by administration in the buccal cavity within the mouth of an individual.

Gene constructs may be administered by means including, but not limited to, traditional syringes, needleless injection devices, or "microprojectile bombardment gene guns". Alternatively, the genetic vaccine may be introduced by various means into cells that are removed from the individual. Such means include, for example, ex vivo transfection, electroporation, microinjection and microprojectile bombardment. After the gene construct is taken up by the cells, they are reimplanted into the individual. It is contemplated that otherwise non-immunogenic cells that have gene constructs incorporated therein can be implanted into the individual even if the vaccinated cells were originally taken from another individual.

According to some embodiments of the present invention, the gene construct is administered to an individual using a needleless injection device. According to some embodiments of the present invention, the gene construct is simultaneously administered to an individual intradermally, subcutaneously and intramuscularly using a needleless injection device. Needleless injection devices are well known and widely available. One having ordinary skill in the art can, following the teachings herein, use needleless injection devices to deliver genetic material to cells of an individual. Needleless injection devices are well suited to deliver genetic material to all tissue. They are particularly useful to deliver genetic material to skin and muscle cells. In some embodiments, a needleless injection device may be used to propel a liquid that contains DNA molecules toward the surface of the individual's skin. The liquid is propelled at a sufficient velocity such that upon impact with the skin the liquid penetrates the surface of the skin, permeates the skin and muscle tissue therebeneath. Thus, the genetic material is simultaneously administered intradermally, subcutaneously and intramuscularly. In some embodiments, a needleless injection device may be used to deliver genetic material to tissue of other organs in order to introduce a nucleic acid molecule to cells of that organ.

The genetic vaccines according to the present invention comprise about 1 nanogram to about 1000 micrograms of nucleic acid, preferably DNA. In some preferred embodiments, the vaccines contain about 10 nanograms to about 800 micrograms of nucleic acid. In some preferred embodiments, the vaccines contain about 0.1 to about 500 micrograms of nucleic acid. In some preferred embodiments, the vaccines contain about 1 to about 350 micrograms of nucleic acid. In some preferred embodiments, the vaccines contain about 25 to about 250 micrograms of nucleic acid. In some preferred embodiments, the vaccines contain about 100 micrograms nucleic acid. One skilled in the art can readily formulate a vaccine comprising any desired amount of nucleic acid.

The genetic vaccines according to the present invention are formulated according to the mode of administration to be used. One having ordinary skill in the art can readily formulate a pharmaceutical composition that comprises a gene construct. Pharmaceutical compositions of the present invention include single genetic constructs encoding either NS3, NS4, or NS5, or any combination thereof. Alternatively, pharmaceutical compositions of the present invention include multiple genetic constructs encoding either NS3, NS4, or NS5, or any combination thereof. In addition, pharmaceutical compositions of the present invention include single or multiple genetic constructs encoding a fragment of NS3, NS4, or NS5, or any combination thereof. In addition, pharmaceutical compositions of the present invention include a single genetic construct encoding fusion proteins of all or any fragment of NS3, NS4, or NS5 proteins. In some cases, an isotonic formulation is used. Generally, additives for isotonicity can include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation. The pharmaceutical preparations according to the present invention are provided sterile and pyrogen free.

The gene constructs of the invention may be formulated with or administered in conjunction with agents that increase uptake and/or expression of the gene construct, referred to herein as "facilitators," by the cells relative to uptake and/or expression of the gene construct by the cells that occurs when the identical genetic vaccine is administered in the absence of such agents. Such agents and the protocols for administering them in conjunction with gene constructs are described in U.S. Pat. Nos. 5,830,876, 5,593,972, 5,739,118 and PCT Patent Application Serial Number PCT/US94/00899 filed Jan. 26, 1994. Examples of such agents include: $CaPO_4$, DEAE dextran, anionic lipids; extracellular matrix-active enzymes; saponins; lectins; estrogenic compounds and steroidal hormones; hydroxylated lower alkyls; dimethyl sulfoxide (DMSO); urea; and benzoic acid esters anilides, amidines, urethanes and the hydrochloride salts thereof such as those of the family of local anesthetics. In addition, the gene constructs are encapsulated within/administered in conjunction with lipids/polycationic complexes. A preferred facilitator is bupivicaine. The compositions can be conveniently administered in unit dosage form and may be prepared by any of the methods well known in the pharmaceutical art, for example, as described in *Remington's Pharmaceutical Sciences* (Mack Pub. Co., Easton, Pa., 1980), the disclosure of which is incorporated herein by reference in its entirety.

In the examples provided below, DNA-based vaccination with plasmids encoding for three different nonstructural proteins of HCV is shown to elicit strong antigen-specific immune responses in both arms of the immune system. After three immunizations, all animals developed detectable antibody responses. In this regard, these, nonstructural proteins are far better antigens to stimulate humoral immune responses compared to previous studies using the structural HCV core structural protein. Tokushige, et al., *Hepatology*, 1996, 24, 14–20; and Geissler, et al., *J. Immunol.*, 1997, 158, 1231–1237. In preferred embodiments, the humoral immune response to the nonstructural proteins may be enhanced by addition of compounds which activate antigen presenting cells, such as, for example, cytokine expressing plasmids, such as IL-2 and GM-CSF. Geissler, et al., *J. Immunol.*, 1997, 158, 1231–1237; and Xiang, *Immunity*, 1995, 129–135. Generation of inflammatory CD4+ T-cell responses with a predominant $T_H1$ phenotype were demonstrated for all three plasmids encoding for NS3, NS4 and NS5. In addition, a strong and specific CD8+ CTL response was generated particularly for NS3 and NS5 with production of lysis values that have previously been shown to induce protection against a variety of pathogens in animal model systems. Tascon, et al., *Nat. Med.*, 1996, 2, 888–892; and Huygen, et al., *Nat. Med.*, 1996, 2, 893–898. Moreover, it was determined if CTL-responses generated by DNA based mutation would protect animals against tumor formation using syngeneic SP2/0 tumor cells stable transfected with a cDNA encoding for NS5 protein. Approximately 60% mice were protected against tumor formation thus indicating the high level CTL activity, produced in vivo by this immunization approach. Further, tumor weight in those animal who developed tumors was significantly reduced compared to notice immunized with mock DNA or recombinant NS5 protein. This model also demonstrates the capability of assessing high level cellular it immune responses against flaviviral nonstructural proteins in an animal model as measured inhibition of tumor growth.

The results disclosed herein teach that DNA-based immunization with gene constructs encoding HCV nonstructural proteins, as described herein, are useful for therapeutic treatment of individuals having HCV as well as for prophylactic vaccines against HCV.

The invention is further illustrated by way of the following examples which are intended to elucidate the invention. These examples are not intended, nor are they to be construed, as limiting the scope of the disclosure.

EXAMPLES

Example 1

Design and Construction of HCV Expression Vectors

The genes encoding for the individual nonstructural proteins were cloned with engineered start and stop codons into an expression plasmid driven by a CMV-promoter and RSV enhancer (pApO31). The expression vector (pcDNA3) containing a selection marker was also used to generate stable SP2/0 transfected cell lines (see FIG. 1A).

As a source of viral genes, a plasmid designated pBRTM/HCV1 covering the full-length ORF of HCV was used to clone into the expression vectors of the present invention. Grakoui, et al., J. Virol., 1993, 67, 1385–1395, the disclosure of which is incorporated herein by reference in its entirety. Alternatively, nucleotide sequences encoding HCV can be obtained from GenBank Accession Numbers X61596 and D16435, the disclosures of which are incorporated herein by reference in their entirety. Constructs pApO31-NS3, pApO31-NS4 and pApO31-NS5 were PCR-cloned after inserting engineered start- and stop-codons as well as restriction enzyme sites using the following primers: for NS3: 5'-GGTCTAGATTGATGGCGCCCATCACGGC-3' (Xba I) (SEQ ID NO:3). 5'-CACACGCGTTCACGTGAC-GACCTCCAGGT-3' (Mlu I) (SEQ ID NO:4), For NS4: 5' GGTCTAGATGAGCACCTGGGTGCTC-3' (Xba I) (SEQ ID NO:5), 5'-CCAGGATCCTCAGCATGGAGTGGTACA-3' (BamHI) (SEQ ID NO:6), and for NS5: 5'-TCAGTCTA-GAATGTCCGGCTCCGGCTCCTGGCTAAGGGA-3' (Xba I) (SEQ ID NO:7), 5'-AGCTACGCGTTCACCGGT-TGGGGAGGAGGT-3' (Mlu I) (SEQ ID NO: 8). After PCR-amplification using a high fidelity PCR System (Boehringer Mannheim, Indianapolis, Ind.), the cDNA fragments were inserted into a plasmid expression vector pApO31 containing an RSV enhancer element and driven by a CMV promoter (Apollon, Malvern Pa.). Constructs were grown in DH5α cells and plasmid DNA was subsequently purified by either 2× cesium chloride centrifugation or Qiagen Giga Kit using the endofree buffer system (Santa Clara, Calif.). Certification of the nonstructural gene inserts was performed by sequencing analysis using standard methods.

For establishing stable NS3, NS4 and NS5 expressing cell lines as target cells for the CTL-assays, the nonstructural protein encoding gene fragments were cloned into the pcDNA3 and pcDNA3.1 Zeo(−) expression vectors (Invitrogen, San Diego) with a neomycin selectable marker. First, a Xba I and Mlu I fragment of NS3 and NS5 was subcloned into the Nhe I/Mlu I site of Litmus-38 vector (New England Biolabs. MA), then cut with EcoR I and Sal I and religated into the EcoR I/Xho I multiple cloning site of pcDNA3 and pcDNA 3.1/Zeo (−), respectively. A Xba I and BamH I fragment containing NS4 was relegated into Litmus-20 (New England Biolabs), recut with Kpn I and EcoR I and subsequently ligated into the pcDNA3 vector. Plasmids were designated pcDNA3-NS3, pcDNA3-NS4 and pcDNA3.1/Zeo(1)-NS5.

One skilled in the art having the DNA sequences encoding any of the HCV nonstructural proteins can design pnmers for preparing any of the gene constructs of the present invention. In addition, nucleotide base substitutions may be made without affecting the binding of the primers. Moreover, the primers may be prepared with endonuclease restriction sites for cloning and ligating purposes, as known to those skilled in the art. Thus, one skilled in the art can prepare any of the gene constructs of the present invention by designing the appropriate primers and performing PCR amplification. The PCR products are ligated into an expression vector.

Plasmids comprising the nucleotide coding sequence for the HCV nonstructural proteins described above each contain the nucleotide coding region for the HCV nonstructural protein placed under the transcriptional control of the CMV promoter and the RSV enhancer element.

Example 2

In Vitro Expression

Figure 1B:
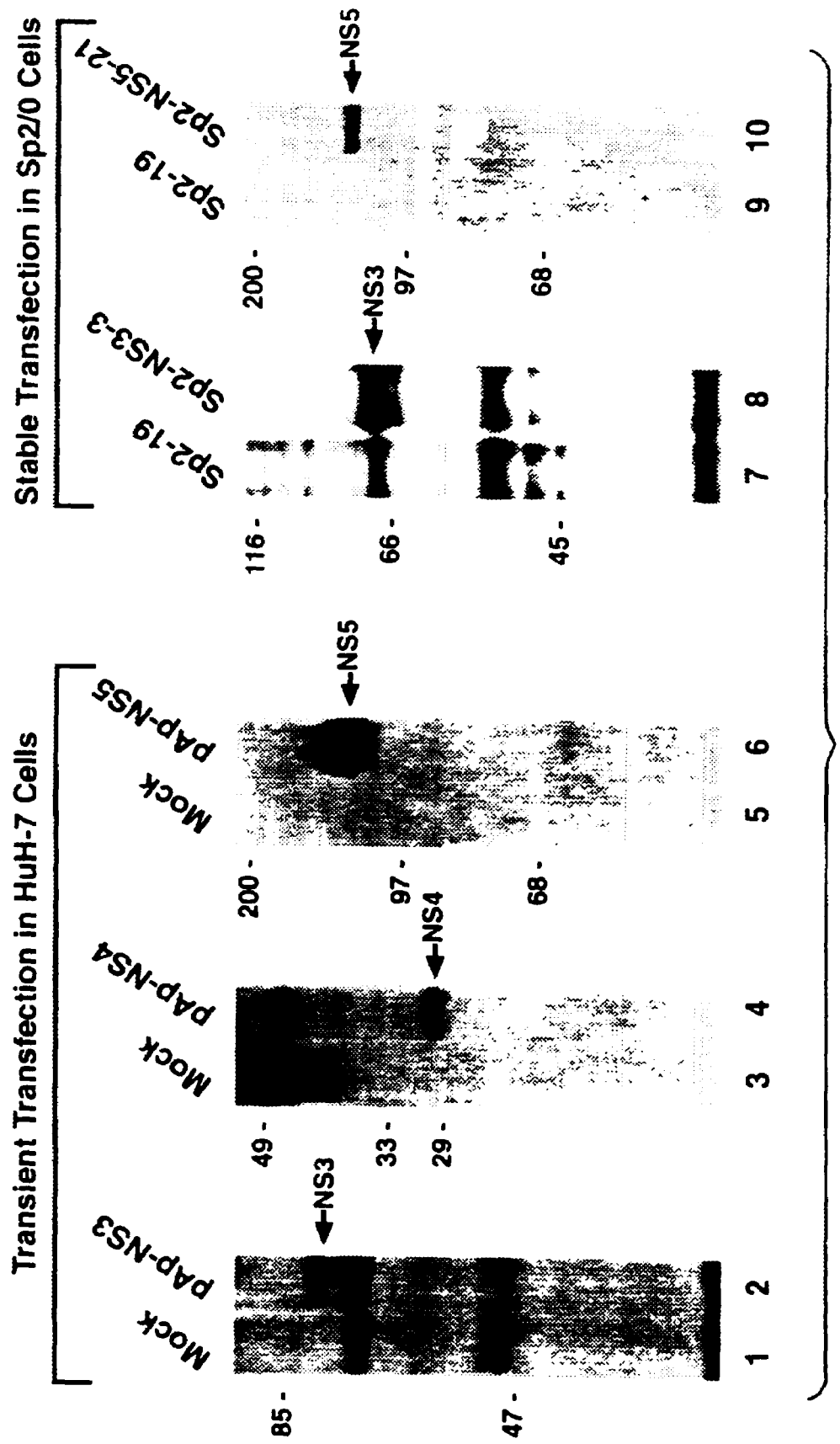
FIG. 1B shows an exemplary autoradiography of the expression of nonstructural proteins following transient transfection of HuH-7 and stable transfection of SP2/0 cells. Lanes 1, 3 and 5 are mock DNA transfected cells and serve as a negative controls (Mock); lanes 2, 4 and 6 show specific bands of about 70 for NS3, about 30 for NS4 and 125 kD for NS5. Lane 7–10 shows SP2/0 cells transfected with nucleic acid constructs containing the genes for NS3, NS4 and NS5, respectively. Lanes 7 and 9 represent cell lysates derived from cells stably expressing HCV-core protein as negative control (SP2–10), whereas lanes 8 and 10 represent specific expression of NS3 and NS5.

The plasmid constructs were sequenced across the gene inserts and protein expression was certified in vitro in HuH-7 cells after transient transfection and in SP2/0 target cells after stable transfection, respectively. Protein bands of about 70 kD for NS3, 30 kD for NS4 and 125 kD for NS5 were found to be expressed within the cell but not secreted into the culture medium (see FIG. 1B).

HuH-7 human hepatoma cell line was transiently transfected with the various constructs by the calcium phosphate method to assess expression levels of HCV nonstructural proteins. In brief, cell lysates were prepared in modified RIPA buffer (0.15 M NaCl 1% NP-40, 50 mM Tris, 0.5% DOC and 1% SDS), after metabolic labeling with $^{35}$S-methionine and cysteine for 4 hours. Cell lysates were precleared with horse serum and then bound to Sepharose A by preincubation overnight with polyclonal antisera WU 110 (NS3), W 148/151 (NS4) and WU 115 (NS5). Grakoui, et al., J. Virol., 1993, 67, 1385–1395, which is incorporated herein by reference in its entirety. After separating the proteins by SDS-PAGE, the gels were dried, followed by autoradiography. The NS5 protein expression was also determined by Western blot and immunofluorescence analysis using a murine mAb (Biogenesis, Sandown, N.H.). To generate stably transfected cell lines expressing NS3, NS4 and NS5, a syngeneic BALB/c mouse myeloma derived cell line SP2/0 was transfected by electroporation with the pcDNA3 plasmid containing the viral gene inserts of interest. Cells growing under G418 selection were cloned by limited dilution (0.3 cell/well) and screened by the methods described above.

pcD3 and pcD3.1 plasmids containing a neomycin or zeomycin resistance gene, respectively, were used for cloning the HCV nonstructural genes and generating stable syngeneic target cell lines. After transient transfection of HuH-7 cells with these constructs and controlling for transfection efficiency with a beta-galactosidase assay, cells were starved for 30 min in methionine and cysteine free medium and labeled for 4 hours with $^{35}$S-methionine and cysteine. Cell lysates were immunoprecipitated with polyclonal rabbit sera specific for the nonstructural proteins and captured by Sepharose A beads, analyzed by SDS-PAGE followed by autoradiography. Lanes 1, 3 and 5 are mock DNA transfected cells and serve as a negative controls (Mock). Lanes 2, 4 and 6 show specific bands of about 70 for NS3, about 30 for NS4 and 125 kD for NS5. (Lane 7–10): SP2/0 cells were transfected with pcD3 based constructs containing the genes for NS3, NS4 and NS5. After antibiotic selection cells were cloned by limiting dilution (0.3 cells/well), and expanded and analyzed either by radioactive labeling and immunoprecipitation of NS3 or Western blot for NS5 as described above. Lane 7 and 9, represent cell lysates derived from cells stable expressing HCV-core protein as negative control (SP2–19), lane 8 and 10 specific expression of NS3 and NS5. These cells were used for in vitro stimulation and as target cells in the CTL-assays.

Example 3

Immunization Protocol

Female BALB/c (h-2d) mice were kept under standard-pathogen-free conditions in the animal facility of the Massachusetts General Hospital. Mice were obtained from Charles River Laboratories (Wilmington, Mass.) and used at the age of 6 to 20 weeks for the in vivo studies. A total of 100 µg of plasmid DNA in 100 µl of 0.9% NaCl were injected two and three times over five different sites into the quadriceps muscle of the mice. Boostered injections were given into the opposite leg every fourteen days. As positive controls for all immunologic experiments, 5 µg of recombinant NS3, NS4 and NS5 nonstructural protein (Mikrogen, Munich) was injected i.p. in CFA at day 0 and boostered with the same amount of protein in 0.05% SDS four and eights weeks later. As negative controls for these experiments empty plasmid vector and recombinant hepatitis B surface antigen (HbsAg) (Energix, Smith Kline Beecham, Philadelphia) were employed. All mice were sacrificed ten days after the last immunization.

Example 4

Measurement of Humoral Immune Responses

Levels of anti-NS3, NS4 and NS5 antibodies were determined in the serum of each immunized animal by an established ELISA technique. In brief, microtiter plates (Falcon, Microtest IIIM Flexible Assay Plate) were coated with the above-described recombinant proteins overnight at 4 C (0.5 µg/well). After blocking with fetal bovine serum (FBS) for 2 hours at 20 C, a 1:50 dilution of mouse serum was added to the plates and incubated at 20 C for an additional hour. After washing 4× with phosphate buffered saline (PBS) containing 0.05% Tween-20, a horseradish peroxidase labeled anti-mouse antibody (Amersham, Arlington Heights, Ill.) was applied at a 1:2000 dilution. Following a 1 hour incubation, plates were washed and substrate was added for color development and read in an automatic reader.

Specific antibody responses directed against all three nonstructural proteins were found in all immunized animals using an enzyme-linked immunosorbent assay (ELISA) following three immunization. No antigen specific immune responses were detected in mice immunized with mock DNA (see FIG. 2A). As positive controls, mice were vaccinated three times intraperitoneally (i.p.) with recombinant NS3, NS4 and NS5 nonstructural proteins in combination with complete Freund's adjuvant (CFA) and, as expected, demonstrated a strong humoral immune response (data not shown).

Figure 2A:
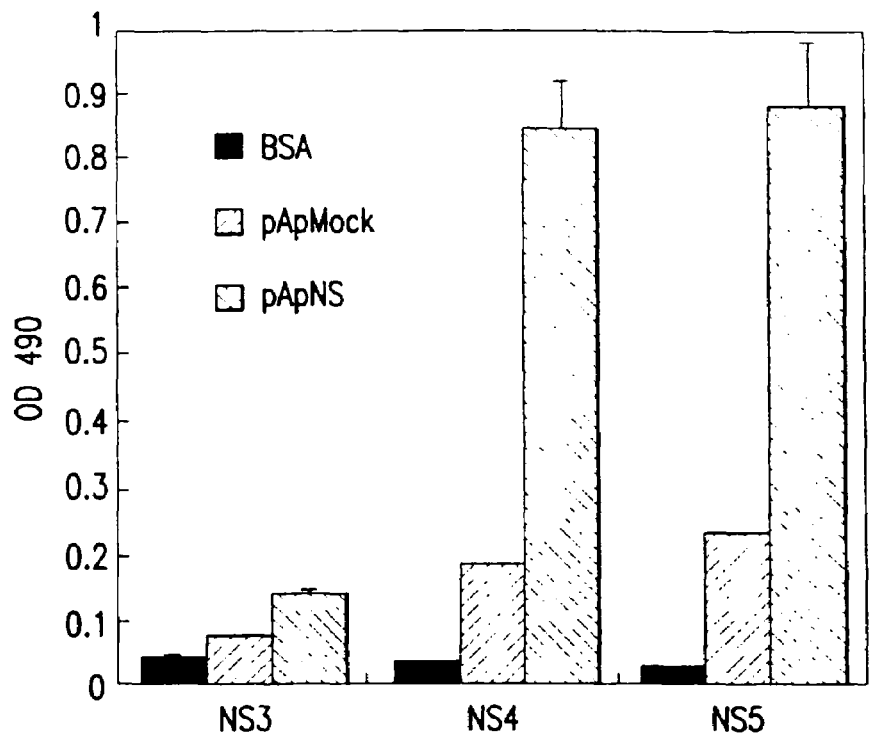
FIG. 2A is a bar graph showing a representative humoral immune response to NS3, NS4 and NS5 generated by DNA-based immunization; serum antibody levels were measured by an ELISA (each group: n=5).
Figure 2B:
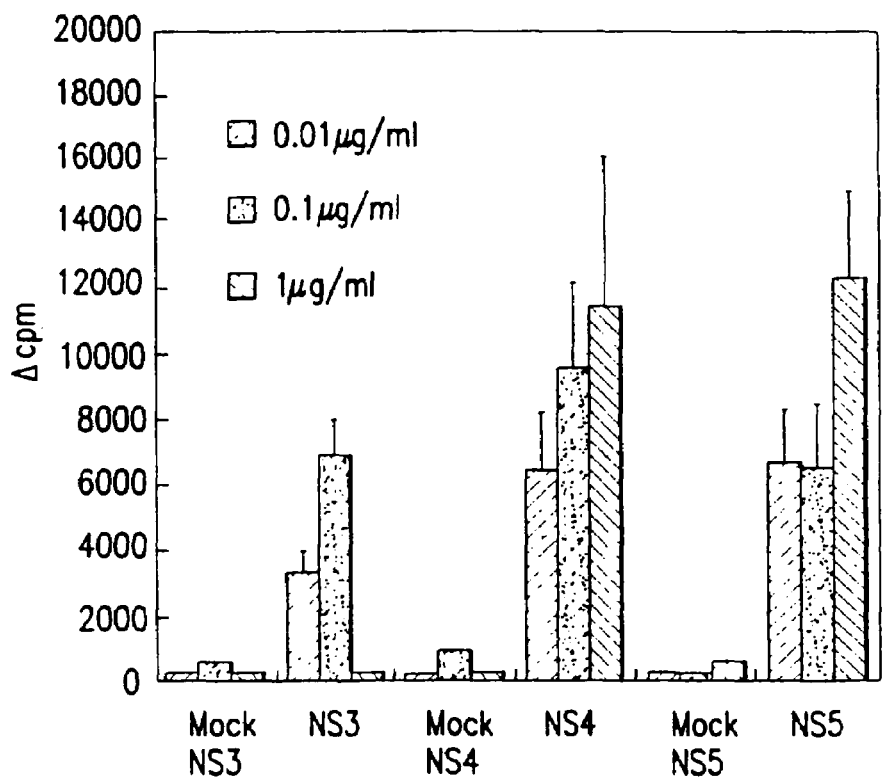
FIG. 2B is a bar graph showing a representative T-cell proliferation measured 3 days after in vitro stimulation with specific or nonspecific recombinant proteins.

FIG. 2A shows humoral immune responses to NS3, NS4 and NS5 generated by DNA-based immunization. Serum antibody levels were measured by an ELISA (each group: n=5). Controls included wells coated with BSA and sera derived from Mock immunized mice. As positive controls mice were immunized i.p. with recombinant proteins (data not shown). FIG. 2B shows T-cell proliferation measured 3 days after in vitro stimulation with specific or nonspecific recombinant proteins. Cells were incubated with $H^3$-thymidine for 18 hours and harvested. The Δ cpm was determined by subtracting background activity (e.g. incubation without antigen). Incubation of cells with 1 µg of recombinant NS3 protein was toxic and therefore no proliferation was seen. Mice immunized with recombinant protein in conjunction with CFA had a 5 to 10 fold higher response (data not shown).

Example 5

Lymphoproliferation and Cytokine Release Assays

Mice were anesthetized with isoflurane (Aerrane, Anaquest, N.J.) and spleen cells were harvested. Erythrocytes were removed by incubation in 0.83% $NH_4Cl$/0.17M Tris pH 7.4, for 5 minutes at 25 C. Spleen cells were washed two times and cultured in triplicate using 96 well round bottom plates at $5\times10^5$ cells/well in 200 µl complete DMEM (Mediatech, Washington, D.C.) containing 10% FBS and 2-mercaptoethanol. Cells were stimulated with recombinant nonstructural protein (NS3, NS4 and NS5) (Mikrogen, Munich) at different concentrations (0, 0.01, 0.1 and 1 µg/ml). As negative controls, effector cells were stimulated with recombinant HCV-core or HbsAg proteins (Energix) at the same concentrations. After stimulation for 3 days, $^3$H-thymidine was added (1 µCi/well). Cells were incubated for additional 18 hours and the $^3$H-thymidine incorporation into DNA was measured after harvesting. Incorporation of radioactivity was corrected for background activity (Δ cpm). For determination of cytokine release effector cells were cultured as described above and IL-2, IL-4 and interferon-γ levels were measured in the culture supernatant by commercial kits according to manufacturer's instructions (Endogen, Boston, Mass.).

In order to investigate cell-mediated immune responses to the nonstructural proteins, spleen cells were harvested and restimulated with either recombinant antigen or antigen expressed by stable transfected cell lines in vitro. Substantial lymphocyte proliferation was induced by all nonstructural proteins at different antigen concentrations as measured by [$^3$H]thymidine incorporation (see FIG. 2B). Immunization with recombinant protein i.p., as a means of generating maximum stimulation, produced a 5–10 fold higher lymphocyte proliferative rate for all three proteins (data not shown). The cytokine profile measured after DNA based immunization demonstrated a classic T1 response with high levels of IFN-γ (FIG. 2C) and IL-2 (FIG. 2D) secreted into the cell culture medium. In contrast, very little IL-4 production was observed after genetic immunization with genes encoding for the HCV nonstructural proteins (FIG. 2E).

Figure 2C:
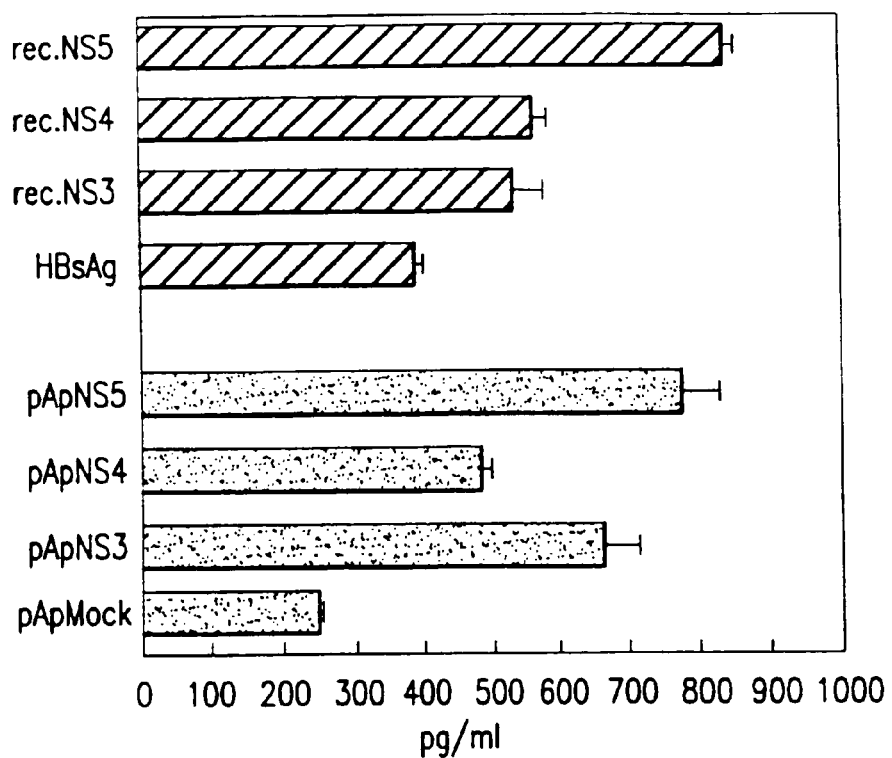
FIGS. 2C, 2D, and 2E are bar graphs showing representative cytokine secretion, IFN-γ, IL-2, and IL-4, respectively, into the supernatant measured after 48 hours of in vitro stimulation.
Figure 2D:
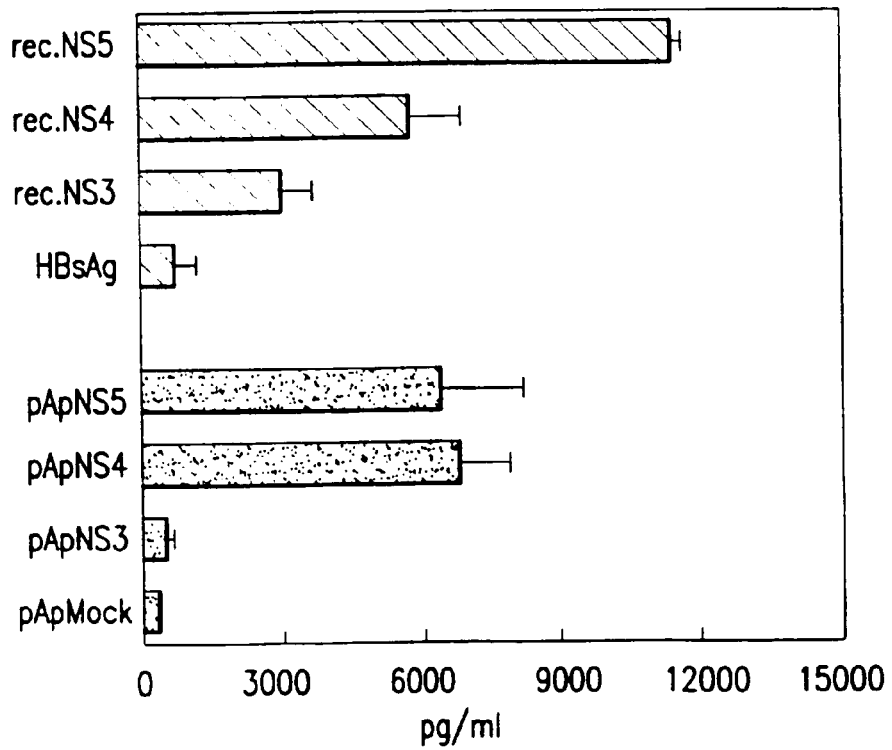
Figure 2E:
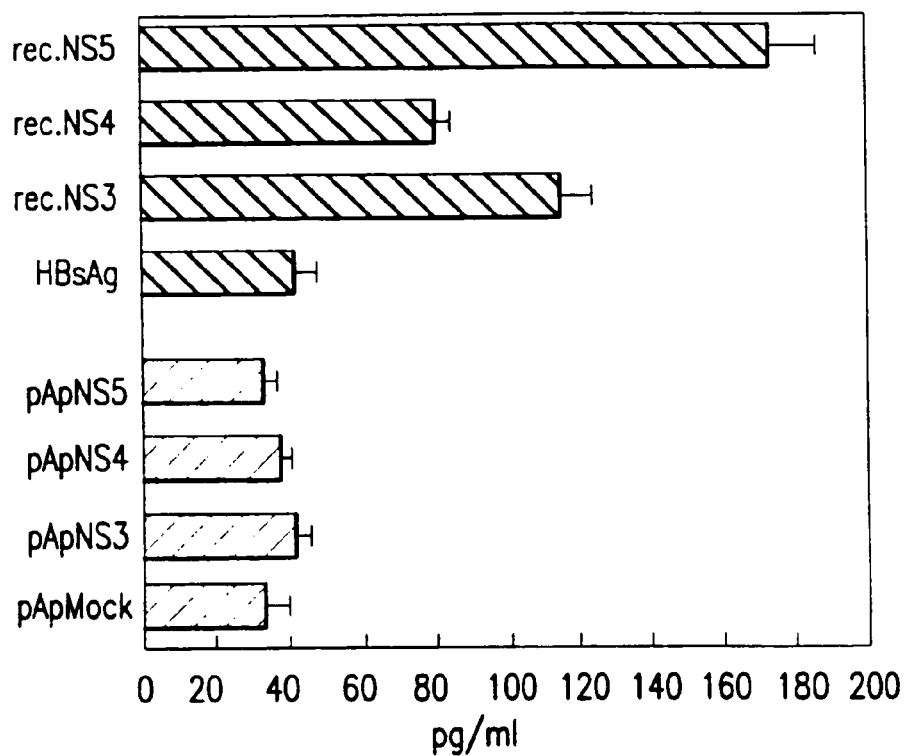

FIGS. 2C, 2D, and 2E show cytokine secretion into the supernatant measured after 48 hours of in vitro stimulation. All DNA-constructs encoding for NS3, NS4 and NS5 proteins induced a $T_H1$-type cytokine profile. For comparison results are shown immunizing mice three times i.p. with recombinant proteins (n=4). As a negative control, mice were immunized with recombinant HbsAg.

Example 6

Cytotoxic T-Lymphocyte Activity

Spleen cells derived from immunized mice were suspended in complete DMEM with 10% FCS and 2-mercaptoethanol ($5\times10^{-5}$M) and analyzed for cytotoxic activity following 5 days of in vitro stimulation. Recombinant murine IL-2 was added once at a concentration of 5 U/ml and responder cells ($4\times10^7$) were co-cultured with $2\times10^6$ irradiated (10,000 rad) syngeneic SP2/0 cells stably expressing either the full length NS3 or NS5 protein (SP2/NS3–3, SP2/NS5–21). After 5 days, cytotoxic effector lymphocyte populations were harvested and a 4 hour $^{51}$Cr-release assay was performed in 96 well round bottom plates using $^{51}$Cr-labeled Sp2/NS3–3 or SP2/NS5–21. Parental SP2/0 or SP2–19 expressing the HCV core protein were used as controls for antigen specificity of lysis and background activity. Assays for CTL activity were performed at lymphocyte effector to target (E:T) ratios of 100:1, 30: 1, 10:1 and 3:1, respectively. T cell depletion experiments were employed by incubating effector cells with either an anti-CD4+ or CD8+ mAb containing hybridoma supernatant GK 1.5 (anti-CD4, rat); 3.155 (anti-CD8, rat)) for 30 min at 4 C, washed, then incubated at 37 C with complement (1:5 dilution of low toxicity rabbit complement (Cedarlane Laboratories, Ontario, Canada)).

Figure 3A:
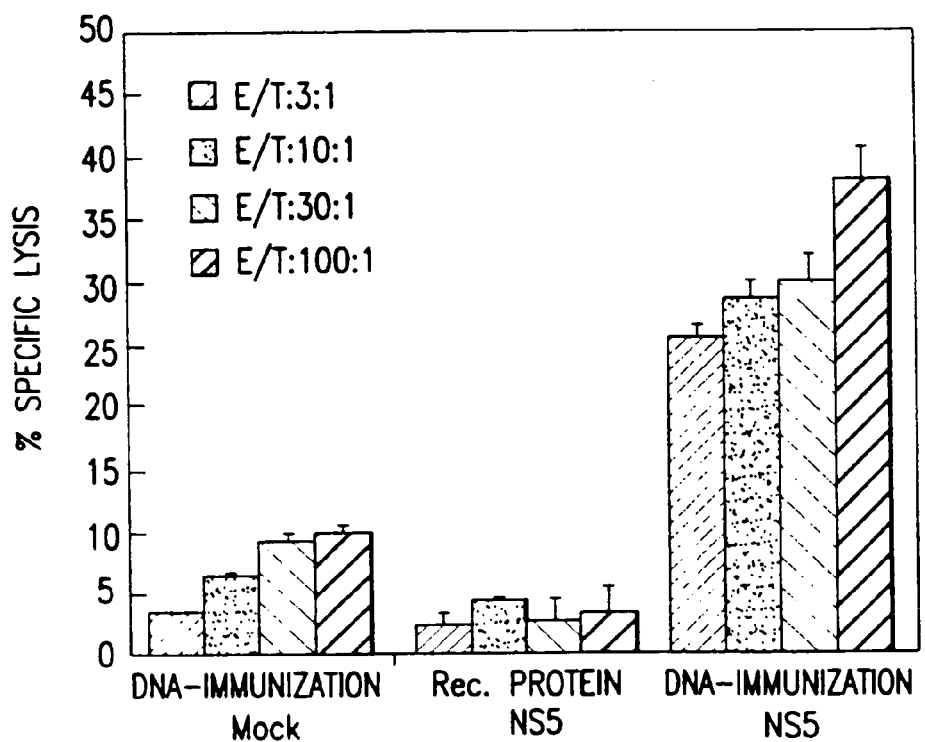
FIGS. 3A and 3B are bar graphs showing a representative cytotoxic T-cell (CTL) response to NS3 and NS 5, respectively, at different effector to target cell ratios (100:1, 30:1, 10:1, 3:1).
Figure 3B:
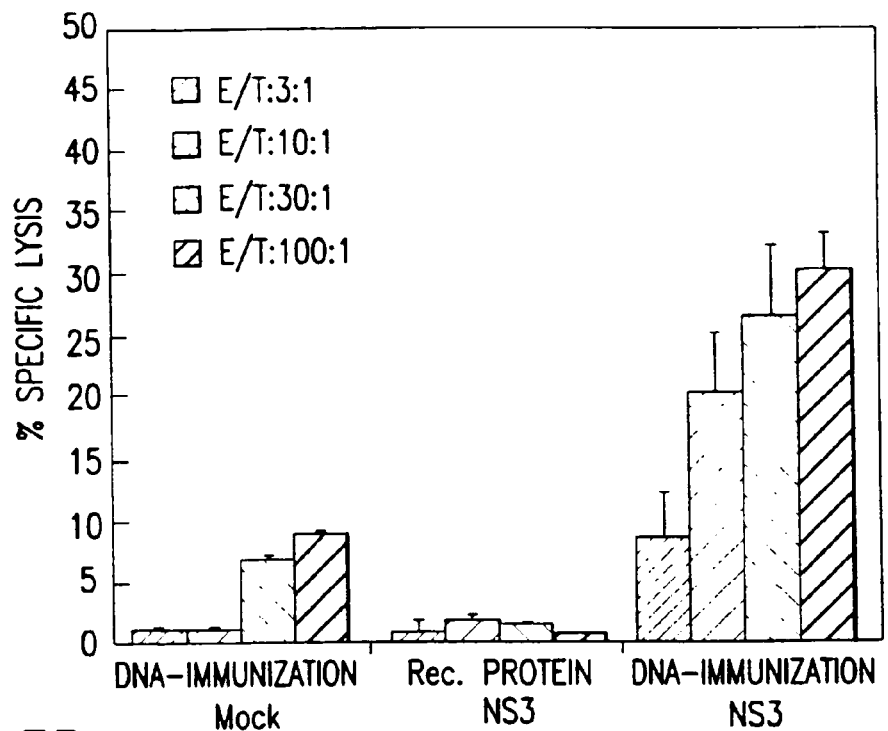
Figure 3C:
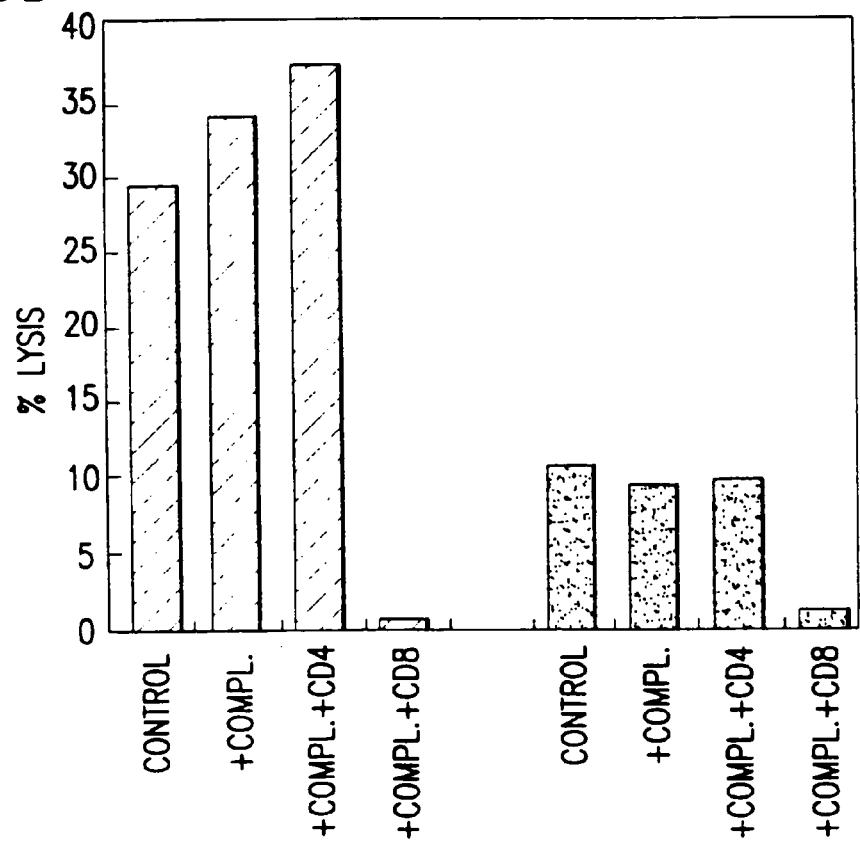
FIG. 3C is a bar graph showing a representative chromium release assay against the stable transfected target cell lines.

Because CTL responses are essential to eliminate virus from infected cells, the ability of splenocytes derived from immunized mice to lyse syngeneic SP2/0 murine myeloma target cells stable transfected and expressing NS3 and NS5 proteins was analyzed in a $^{51}$Cr-release assay. The NS3 and NS5 immunized mice exhibited a strong and specific cytotoxic T-cell response after 5 days of in vitro stimulation, whereas low activity was observed against SP2/0 or SP2–19 (stable expressing HCV-core protein) cells used as controls for target cell specificity (FIGS. 3A and 3B). To demonstrate the phenotype of cells producing the specific lysis, splenocytes were incubated with CD8+ or CD4+ reactive monoclonal antibodies (mAbs) in the presence of complement. The cytotoxic activity was mediated by CD8+ cells (FIG. 3C). We were unable to establish SP2/0 cell lines stable expressing NS4 protein and therefore CTL activity was not measured against this HCV nonstructural protein.

FIG. 3 shows cytotoxic T-cell (CTL) response to NS3 (A) and NS5 (B) at different effector to target cell ratios (100:1, 30:1, 10:1, 3:1). Splenocytes were incubated in vitro with irradiated stable NS3 and NS5 expressing mouse myeloma cells for five days (n=5). Subsequently, CTL activity was determined in a 4 hour $Cr^{51}$ release assay against the stable transfected target cell lines. Background activity against SP2/0 or SP2–19 (expressing HCV-core) was subtracted to reveals specific lysis values. FIG. 3C shows that in T-cell depletion experiments (n=3), cells were incubated for 30 min on ice with anti-CD8+ or CD4+ mAbs and followed by 30 min incubation 37 C with complement. Controls cells were incubated without complement and anti-CD8+ or anti-CD4+ mAbs. Background activity was determined against SP2–19 cells as a nonrelevant negative control cell line that is stable transfected with a HCV core expression construct.

Example 7

Assessment of Cytotoxic T-Lymphocyte Activity In Vivo

CTL experiments have been extremely difficult to perform because no one has been able to establish, until now, stable cell lines expressing the nonstructural proteins for use in CTL activity. Mice were immunized intramuscularly (i.m.) three times with either mock DNA or pApNS5 vector. Some animals were also immunized i.p. with recombinant NS5 protein or a combination of the both. Recombinant protein (5 µg i.p.) was given as mixture of NS5–4 (aa 2622–2868) and NS5–12 (aa 2007–2268) E. coli expressed protein (Mikrogen, Munich, Germany) covering parts of HCV-NS5a and HCV NS5b regions (about 50% of full length NS5). One week after the last immunization with the various plasmid constructs or recombinant protein, $2\times10^6$ syngeneic SP2/0 derived cells stable expressing NS5 were washed and resuspended in 200 µl PBS an inoculated subcutaneously into the night flank. SP2/0 cells were either expressing HCV NS5 (SP2/NS5–21) or HCV core protein SP2/19). In this animal model, tumor formation was assessed 15 days after inoculation and the number of animals with tumors and tumor weight was determined.

Figure 4B:
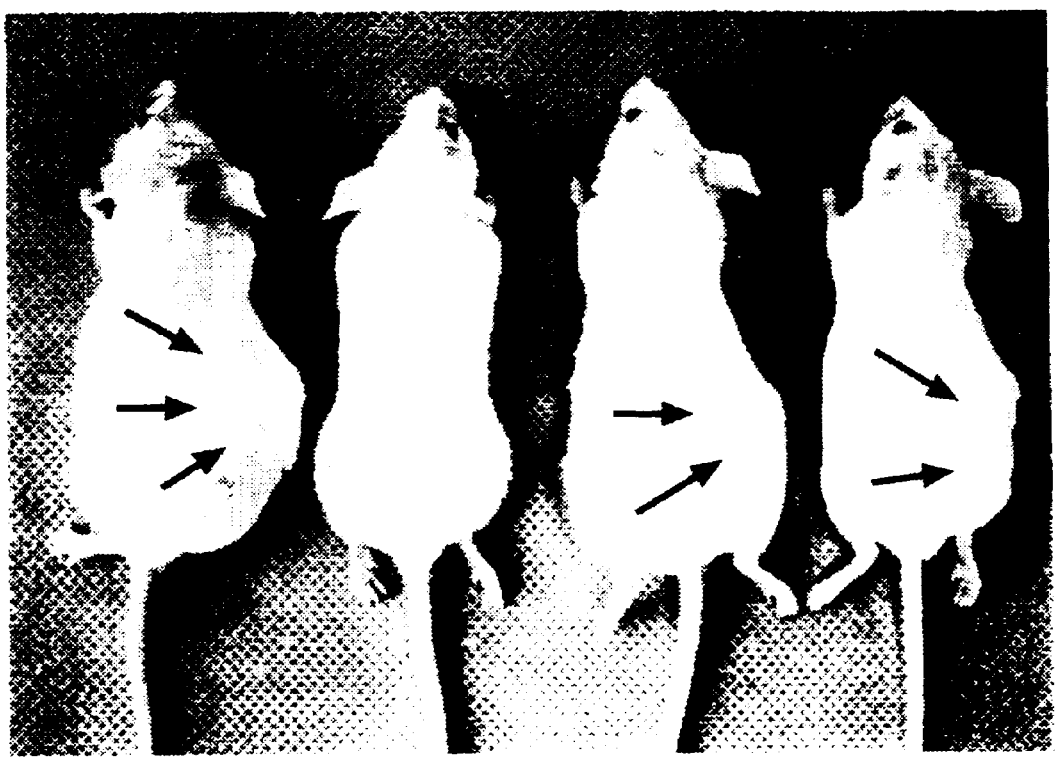
FIG. 4B is a photograph showing, from left to right, animals immunized with 1) mock DNA and challenged with SP2/NS5–21 cells; 2) pApNS5 and challenged with SP2/NS5–21 cells; 3) pApNS5 and challenged with SP2–19, (stable expressing HCV core); and 4) animal immunized three times i.p. with recombinant NS5 protein and challenged with SP2/NS5–21 cells.

Only 40% of mice immunized with mock DNA and, challenged with a NS5 expressing murine myeloma cell line (SP2/NS5–21) developed tumors after 15 days. Moreover, tumor size was less as determined by measurement of tumor weight as compared to mice immunized with mock DNA or recombinant NS5 protein or mice immunized with the same syngeneic SP2/0 cell line expressing a different HCV structural protein (HCV-core) as a control (FIGS. 4A and 4B). Indeed, 90–100% of mice immunized with mock DNA or challenged with SP2–19 cells demonstrated tumor formation, thus demonstrating the specificity of the CTL activity in this small animal tumor model. It is important to emphasize that immunization with recombinant NS5 protein in CFA does not protect animals against tumor formation. To assess the effect of a combination of DNA-based immunization and recombinant protein vaccination, one group of animals was immunized with both. There was partial protection against tumor formation but this regimen was not as effective as animals immunized three times with DNA encoding for NS5 protein (FIG. 4A).

FIG. 4A shows representative results obtained from a tumor model to assess CTL activity. Mice were immunized three times i.m. with either pApNS5 or Mock DNA (100 µg) or recombinant NS5 protein i.p. (5 µg). The final group received a combination of DNA-immunization and recombinant protein. Fifteen days after tumor challenge with SP2NS5–21 or SP2–10 cells, the number of mice that developed tumors was determined and the tumor weight was measured. FIG. 4B, from left to right, shows animal immunized with Mock DNA and challenged with SP2/NS5–21 cells; animal immunized with pApNS5 and challenged with SP2/NS5–21 cells; animal immunized with pApNS5 and challenged with SP2–19, (stable expressing HCV core); and animal immunized three times i.p. with recombinant NS5 protein and challenged with SP2/NS5–21 cells. Large tumor formed on the right flank in the first, third and fourth animal, but not in the second, which was immunized with pApNS5 and challenged with the NS5 stable expressing murine myeloma cell line.

What is claimed is:

1. A recombinant nucleic acid molecule consisting of a nucleotide sequence encoding hepatitis C virus nonstructural proteins NS3, NS4 and NS5, wherein said nucleotide sequence is operably linked to regulatory elements, said regulatory elements comprising a promoter, enhancer, polyadenylation sequence, and a hepatitis C virus 5' untranslated region (5'-UTR).

2. The recombinant nucleic acid molecule of claim 1 wherein said non-structural proteins NS3, NS4 or NS5 are at least 50 amino acids in length.

3. The recombinant nucleic acid molecule of claim 1 wherein said promoter is a cytomegalovirus promoter and said enhancer is a Rous Sarcoma Virus enhancer.

4. A recombinant host cell comprising a nucleic acid molecule of claim 1.

5. A method of inducing an immune response against hepatitis C virus in a human uninfected by hepatitis C virus comprising administering to said human a recombinant nucleic acid molecule consisting of a nucleotide sequence encoding hepatitis C virus nonstructural proteins NS3, NS4 and NS5, wherein said nucleotide sequence is operably linked to regulatory elements, said regulatory elements comprising a promoter, enhancer, polyadenylation sequence, and a hepatitis C virus 5' untranslated region (5'-UTR), in an amount effective to induce an immune response against hepatitis C virus.

6. The method of claim 5 wherein said non-structural proteins NS3, NS4 or NS5 are at least 50 amino acids in length.

7. The method of claim 5 wherein said promoter is a cytomegalovirus promoter and said enhancer is a Rous Sarcoma Virus enhancer.

8. The method of claim 5 wherein said immune response comprises a cellular response.

9. The method of claim 5 wherein said immune response comprises a humoral response.

10. The method of claim 5 wherein said recombinant nucleic acid molecule is in a pharmaceutical composition comprising a pharmaceutically acceptable carrier or diluent.

11. The method of claim 10 wherein said pharmaceutical composition further comprises a facilitator.

12. The method of claim 11 wherein said facilitator is bupivacaine.

13. The recombinant nucleic acid molecule of claim 1, wherein said 5'-UTR comprises at least the 9 most 3' nucleotides of a 5'-UTR of hepatitis C virus.

* * * * *

SEQUENCE LISTING

<160> NUMBER OF SEQ ID NOS: 8

<210> SEQ ID NO 1
<211> LENGTH: 9
<212> TYPE: DNA
<213> ORGANISM: Artificial Sequence
<220> FEATURE:
<223> OTHER INFORMATION: Description of Artificial Sequence: synthetic
      sequence

<400> SEQUENCE: 1 gccgccatg                                                                9

<210> SEQ ID NO 2
<211> LENGTH: 341
<212> TYPE: DNA
<213> ORGANISM: Artificial Sequence
<220> FEATURE:
<223> OTHER INFORMATION: Description of Artificial Sequence: synthetic
      sequence

<400> SEQUENCE: 2
gccagccccc gattggggc gacactccac catagatcac tccctgtga ggaactactg         60 tcttcacgca gaaagcgtct agccatggcg ttagtatgag tgtcgtgcag cctccaggac     120
cccccctccc gggagagcca tagtggtctg cggaaccggt gagtacaccg gaattgccag     180
gacgaccggg tcctttcttg gatcaacccg ctcaatgcct ggagatttgg gcgtgccccc     240
gcgagactgc tagccgagta gtgttgggtc gcgaaaggcc ttgtggtact gcctgatagg     300
gtgcttgcga gtgccccggg aggtctcgta gaccgtgcac c                         341

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: synthetic
      sequence

<400> SEQUENCE: 3
ggtctagatt gatggcgccc atcacggc                                          28

<210> SEQ ID NO 4
<211> LENGTH: 29
<212> TYPE: DNA
<213> ORGANISM: Artificial Sequence
<220> FEATURE:
<223> OTHER INFORMATION: Description of Artificial Sequence: synthetic
      sequence

<400> SEQUENCE: 4
cacacgcgtt cacgtgacga cctccaggt                                         29

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: synthetic
      sequence

<400> SEQUENCE: 5
ggtctagatg agcacctggg tgctc                                             25

-continued

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence: synthetic sequence

<400> SEQUENCE: 6
ccaggatcct cagcatggag tggtaca 27

<210> SEQ ID NO 7
<211> LENGTH: 39
<212> TYPE: DNA
<213> ORGANISM: Artificial Sequence
<220> FEATURE:
<223> OTHER INFORMATION: Description of Artificial Sequence: synthetic sequence

<400> SEQUENCE: 7
tcagtctaga atgtccggct ccggctcctg gctaaggga 39

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: synthetic sequence

<400> SEQUENCE: 8
agctacgcgt tcaccggttg gggaggaggt 30